(12) United States Patent
Sanz Pamplona et al.

(10) Patent No.: US 9,645,150 B2
(45) Date of Patent: May 9, 2017

(54) METHOD FOR DETERMINING THE RISK OF DEVELOPING BRAIN METASTASIS, AND A KIT TO CARRY OUT SAID METHOD

(75) Inventors: Rebeca Sanz Pamplona, Barcelona (ES); Angels Sierra Jimenez, Barcelona (ES); Baldomero Oliva Miguel, Barcelona (ES); Victor Raul Moreno Aguado, Barcelona (ES); Juan Miguel Gil Gil, Barcelona (ES)

(73) Assignee: Angels Sierra Jimenez, Sabadell, Barcelona (ES)

( * ) Notice: Subject to any disclaimer, the term of this patent is extended or adjusted under 35 U.S.C. 154(b) by 0 days.

(21) Appl. No.: 13/377,468

(22) PCT Filed: Jun. 8, 2010

(86) PCT No.: PCT/EP2010/057947
§ 371 (c)(1),
(2), (4) Date: Mar. 8, 2012

(87) PCT Pub. No.: WO2010/142651
PCT Pub. Date: Dec. 16, 2010

(65) Prior Publication Data
US 2012/0157338 A1 Jun. 21, 2012

(30) Foreign Application Priority Data
Jun. 10, 2009 (ES) .................................. 200930294

(51) Int. Cl.
C12Q 1/68 (2006.01)
G01N 33/567 (2006.01)
G01N 33/574 (2006.01)

(52) U.S. Cl.
CPC . *G01N 33/57407* (2013.01); *G01N 33/57415* (2013.01); *G01N 2333/50* (2013.01)

(58) Field of Classification Search
None
See application file for complete search history.

(56) References Cited

U.S. PATENT DOCUMENTS

| | | | | |
|---|---|---|---|---|
| 5,188,964 A * | 2/1993 | McGuire | ................ | C07K 14/00 252/408.1 |
| 7,252,821 B2 * | 8/2007 | Young | ................ | A61K 49/0058 424/133.1 |
| 2007/0178090 A1 * | 8/2007 | Sukumar | ................ | A61K 38/17 424/144.1 |
| 2008/0279853 A1 * | 11/2008 | Burkly | ................ | C07K 16/2875 424/135.1 |
| 2009/0074762 A1 * | 3/2009 | Culp | ................ | C07K 16/2878 424/133.1 |

OTHER PUBLICATIONS

Escobar et al (J of Pediatric Surgery, 2005: vol. 40, pp. 349-358).*
Gaedcke et al in Predominance of the basal type and HER-2/neu type in brain metastasis from breast cancer. (Modern Pathology:Aug. 2007 vol. 20, No. 8, pp. 864-870).*
Winkles et al (Cancer Letters vol. 235, 2006, pp. 11-17).*
European Patent No. EP 1 365 242 A1 (MTM LAB AG [DE]); published Nov. 26, 2003.
European Patent No. EP 1 961 825 A1 (Inst Nat Sante Rech Med [FR]); published Aug. 27, 2008.
PCT International Application Publication No. WO 01/81423 A1 (Fenning Biomed GMBH DR [DE]; Terness Peter [DE]; Kleist Christian [DE]; published Nov. 1, 2001, of PCT International Application No. PCT/EP2001/04382, filed Apr. 18, 2001.
Esseghir Selma et al., "Identification of NTN4, TRA1, and STC2 as prognostic markers in breast cancer in a screen for signal sequence encoding proteins", Clinical Cancer Research: An Official Journal of the American Association for Cancer Research Jun. 1, 2007 Lnkd-Pubmed:17545519, vol. 13, No. 11, Jun. 1, 2007, pp. 3164-3173.
Tosoni A. et al., "Chemotherapy in breast cancer patients with brain metastases: Have new chemotherapic agents changed the clinical outcome?", Critical Reviews in Oncology/Hematology, Elsevier Science Ireland Ltd., Limerick, vol. 68, No. 3, Dec. 1, 2008, pp. 212-221.
Tran Nhan L. et al.,, "The human Fn14 receptor gene is up-regulated in migrating glioma cells in vitro and overexpressed in advanced glial tumors", American Journal of Pathology, vol. 162, No. 4, Apr. 2003, pp. 1313-1321.
Tran Nhan L. et al., "Increased fibroblast growth factor-inducible 14 expression levels promote glioma cell invation via Rac1 and nuclear factor-kappa B and correlate with poor patient outcome", Cancer Research, vol. 66, No. 19, Oct. 2006, pp. 9535-9542.
Martin Berta et al., "Biological pathways contributing to organ-specific phenotype of brain metastatic cells", Journal of Proteome Research, vol. 7, No. 3, Mar. 2008, pp. 908-920.
Sanz R. et al., "Biological functions of brain metastasis from breast cancer", European Journal of Cancer. Supplement, Pergamon, Oxford, vol. 4, No. 2, Mar. 1, 2006, p. 165.
Winkles Jeffrey A et al., "Role of TWEAK and Fn14 in tumor biology", Frontiers in Bioscience, Frontiers in Bioscience, NY, US vol. 12, Jan. 1, 2007, pp. 2761-2771.

(Continued)

*Primary Examiner* — Catherine S Hibbert
(74) *Attorney, Agent, or Firm* — Gary J. Gershik; Cooper & Dunham LLP

(57) ABSTRACT

The method comprises: (a) isolating a sample from the breast tumor; (b) determining the level of expression of GRP94, FN14 or both in the sample, and (c) comparing said level with the level of said gene(s) in a control sample, wherein if it is detected an overexpression of said gene(s), in respect of the control sample, it is indicative of the risk for developing brain metastasis.

The kit to carry out the method of the invention comprises appropriate means to determine the level of expression of each one of the markers.

Both, the method and kit provides accurate information about the risk of developing brain metastasis in an early state, which can lead to a reduction of the incidence of breast cancer brain metastasis.

16 Claims, 7 Drawing Sheets

(56) References Cited

OTHER PUBLICATIONS

International Search Report issued by the International Searching Authority (ISA/O.E.P.M.) on Jan. 3, 2011 in connection with International Application No. PCT/EP2010/057947.
Al-Shahrour, F. et al., "FatiGO: a web tool for finding significant associations of Gene Ontology terms with groups of genes", Bioinformatics, 2004, vol. 20, No. 4, pp. 578-580.
Aragues, R. et al., "PIANA: protein interactions and network analysis", Bioinformatics, 2006, vol. 22, No. 8, pp. 1015-1017.
Aragues, R. et al., "Predicting cancer involvement of genes from heterogeneous data", BMC Bioinformatics, 2008, vol. 9, No. 172, pp. 1-18.
Cockell, S.J. et al., "Structure-based evaluation of *in silico* predictions of protein-protein interactions using Comparative Docking", Bioinformatics, 2007, vol. 23, No. 5, pp. 573-581.
Dawelbait, G. et al., "Structural templates predict novel protein interactions and targets from pancreas tumour gene expression data", Bioinformatics, 2007, vol. 23, pp. i115-i124.
Fernández, P.L. et al., "Tissue macroarrays ("microchops") for gene expression analysis", Virchows Arch, 2001, vol. 438, pp. 591-594.
Gentleman, R. et al., "Bioconductor: open software development for computational biology and bioinformatics", Genome Biology, 2004, vol. 5, issue 10, article R80 (R80.1-R80.16).
Ginestier, C. et al., "Distinct and Complementary Information Provided by Use of Tissue and DNA Microarrays in the Study of Breast Tumor Markers", American Journal of Pathology, 2002, vol. 161, No. 4, pp. 1223-1233.
Irizarry, R.A. et al., "Exploration, normalization, and summaries of high density oligonucleotide array probe level data", Biostatistics, 2003, vol. 4, No. 2, pp. 249-264.
Jacquemier, J. et al., "Protein Expression Profiling Identifies Subclasses of Breast Cancer and Predicts Prognosis", Cancer Research, 2005, vol. 65, No. 3, pp. 767-779.
Kelso, R. et al., "Flytrap, a database documenting a GFP protein-trap insertion screen in *Drosophila melanogaster*", Nucleic Acids Research, 2004, vol. 32, Database issue, pp. D418-D420.
Klein, A. et al., "Identification of brain- and bone- specific breast cancer metastasis genes", Cancer Letters, 2009, vol. 276, pp. 212-220.
Landemaine, T. et al., "A Six-Gene Signature Predicting Breast Cancer Lung Metastasis", Cancer Research, 2008, vol. 68, pp. 6092-6099.
Li, F. et al., "Identification and Analysis of Signaling Networks Potentially Involved in Breast Carcinoma Metastasis to the Brain", PLOS ONE 2011, vol. 6, issue 7, e21977 (1-14).
Lönnstedt, I. and Terry Speed, "Replicated Microarray Data", Statistica Sinica, 2002, vol. 12, pp. 31-46.
Martin, B. et al., "Functional Clustering of Metastasis Proteins Describes Plastic Adaptation Resources of Breast-Cancer Cells to New Microenvironments", Journal of Proteome Research, 2008, vol. 7, pp. 3242-3253.
Martin, B. et al., "Biological Pathways Contributing to Organ-Specific Phenotype of Brain Metastatic Cells", Journal of Proteome Research, 2008, vol. 7, pp. 908-920.
Nevins, J.R. et al,, "Towards integrated clinico-genomic models for personalized medicine: combining gene expression signatures and clinical factors in breast cancer outcomes prediction", Human Molecular Genetics, 2003, vol. 12, Review Issue 2, pp. R153-R157.
Pagel, P. et al., "The MIPS mammalian protein-protein interaction database", Bioinformatics, 2005, vol. 21, No. 6, pp. 832-834.
Peri, S. et al., "Human protein reference database as a discovery resource for proteomics", Nucleic Acids Research, 2004, vol. 32, Database Issue, pp. D497-D501.
Rual, J.F. et al., "Towards a proteome-scale map of the human protein-protein interaction network", Nature, 2005, vol. 437, pp. 1173-1178.
Salwinski, L. et al., "The Database of Interacting Proteins: 2004 Update", Nucleic Acids Research, 2004, vol. 32, Database Issue, pp. D449-D451.
Schackert, G. et al., "Unique Patterns of Brain Metastasis Produced by Different Human Carcinomas in Athymic Nude Mice", Int. J. Cancer, 1989, vol. 44, pp. 892-897.
Schouten, L.J. et al., "Incidence of Brain Metastases in a Cohort of Patients with Carcinoma of the Breast, Colon, Kidney, and Lung and Melanoma", Cancer, 2002, vol. 94, pp. 2698-2705.
Stelzl, U. et al., "A Human Protein-Protein Interaction Network: A Resource for Annotating the Proteome", Cell, 2005, vol. 122, pp. 957-968.
Tosoni, A. et al., "Chemotherapy in breast cancer patients with brain metastases: Have new chemotherapic agents changed the clinical outcome?", Critical reviews in oncology/hematology, 2008, vol. 68, No. 3, pp. 212-221.
Van't Veer, L.J. et al., "Gene expression profiling predicts clinical outcome of breast cancer", Nature, 2002, vol. 415, pp. 530-536.
Willis, A.L. et al., "The Fibroblast Growth Factor—Inducible 14 Receptor is Highly Expressed in HER2-Positive Breast Tumors and Regulates Breast Cancer Cell Invasive Capacity", Molecular Cancer Research, 2008, vol. 6, No. 5, pp. 725-734.
Winkles, J.A., "TWEAK and Fn14: New molecular targets for cancer therapy?", Cancer Letters, 2006, vol. 235, pp. 11-17.
Zhang, R.D. et al., "Relative Malignant Potential of Human Breast Carcinoma Cell Lines Established from Pleural Effusions and a Brain Metastasis", Invasion Metastasis, 1991, vol. 11, pp. 204-215.

* cited by examiner

FIG. 4

P14625 (ENPL_HUMAN)

```
            10         20         30         40         50         60
    MRALWVLGLC CVLLTFGSVR ADDEVDVDGT VEEDLGKSRE GSRTDDEVVQ REEEAIQLDG 70         80         90        100        110        120
    LNASQIRELR EKSEKFAFQA EVNRMMKLII NSLYKNKEIF LRELISNASD ALDKIRLISL 130        140        150        160        170        180
    TDENALSGNE ELTVKIKCDK EKNLLHVTDT GVGMTREELV KNLGTIAKSG TSEFLNKMTE 190        200        210        220        230        240
    AQEDGQSTSE LIGQFGVGFY SAFLVADKVI VTSKHNNDTQ HIWESDSNEF SVIADPRGNT 250        260        270        280        290        300
    LGRGTTITLV LKEEASDYLE LDTIKNLVKK YSQFINFPIY VWSSKTETVE EPMEEEEAAK 310        320        330        340        350        360
    EEKEESDDEA AVEEEEEEKK PKTKKVEKTV WDWELMNDIK PIWQRPSKEV EEDEYKAFYK 370        380        390        400        410        420
    SFSKESDDPM AYIHFTAEGE VTFKSILFVP TSAPRGLFDE YGSKKSDYIK LYVRRVFITD 430        440        450        460        470        480
    DFHDMMPKYL NFVKGVVDSD DLPLNVSRET LQQHKLLKVI RKKLVRKTLD MIKKIADDKY 490        500        510        520        530        540
    NDTFWKEFGT NIKLGVIEDH SNRTRLAKLL RFQSSHHPTD ITSLDQYVER MKEKQDKIYF 550        560        570        580        590        600
    MAGSSRKEAE SSPFVERLLK KGYEVIYLTE PVDEYCIQAL PEFDGKRFQN VAKEGVKFDE 610        620        630        640        650        660
    SEKTKESREA VEKEFEPLLN WMKDKALKDK IEKAVVSQRL TESPCALVAS QYGWSGNMER 670        680        690        700        710        720
    IMKAQAYQTG KDISTNYYAS QKKTFEINPR HPLIRDMLRR IKEDEDDKTV LDLAVVLFET 730        740        750        760        770        780
    ATLRSGYLLP DTKAYGDRIE RMLRLSLNID PDAKVEEEPE EEPEETAEDT TEDTEQDEDE 790        800
    EMDVGTDEEE ETAKESTAEK DEL
```

FIG. 5

Q9NP84 (TNR12_HUMAN)

```
         10         20         30         40         50         60
MARGSLRRLL RLLVLGLWLA LLRSVAGEQA PGTAPCSRGS SWSADLDKCM DCASCRARPH 70         80         90        100        110        120
SDFCLGCAAA PPAPFRLLWP ILGGALSLTF VLGLLSGFLV WRRCRRREKF TTPIEETGGE

GCPAVALIQ
```

FIG. 6

Q96NT2 (TRAF2_HUMAN)
Q12933

```
         10         20         30         40         50         60
MAAASVTPPG SLELLQPGFS KTLLGTKLEA KYLCSACRNV LRRPFQAQCG HRYCSFCLAS 70         80         90        100        110        120
ILSSGPQNCA ACVHEGIYEE GISILESSSA FPDNAARREV ESLPAVCPSD GCTWKGTLKE 130        140        150        160        170        180
YESCHEGRCP LMLTECPACK GLVRLGEKER HLEHECPERS LSCRHCRAPC CGADVKAHHE 190        200        210        220        230        240
VCPKFPLTCD GCGKKKIPRE KFQDHVKTCG KCRVPCRFHA IGCLETVEGE KQQEHEVQWL 250        260        270        280        290        300
REHLAMLLSS VLEAKPLLGD QSHAGSELLQ RCESLEKKTA TFENIVCVLN REVERVAMTA 310        320        330        340        350        360
EACSRQHRLD QDKIEALSSK VQQLERSIGL KDLAMADLEQ KVLEMEASTY DGVFIWKISD 370        380        390        400        410        420
FARKRQEAVA GRIPAIFSPA FYTSRYGYKM CLRIYLNGDG TGRGTHLSLF FVVMKGPNDA 430        440        450        460        470        480
LLRWPFNQKV TLMLLDQNNR EHVIDAFRPD VTSSSFQRPV NDMNIASGCP LFCPVSKMEA 490        500
KNSYVRDDAI FIKAIVDLTG L
```

FIG. 7

P04626 (ERBB2_HUMAN)

```
         10         20         30         40         50         60
 MELAALCRWG LLLALLPPGA ASTQVCTGTD MKLRLPASPE THLDMLRHLY QGCQVVQGNL 70         80         90        100        110        120
 ELTYLPTNAS LSFLQDIQEV QGYVLIAHNQ VRQVPLQRLR IVRGTQLFED NYALAVLDNG 130        140        150        160        170        180
 DPLNNTTPVT GASPGGLREL QLRSLTEILK GGVLIQRNPQ LCYQDTILWK DIFHKNNQLA 190        200        210        220        230        240
 LTLIDTNRSR ACHPCSPMCK GSRCWGESSE DCQSLTRTVC AGGCARCKGP LPTDCCHEQC 250        260        270        280        290        300
 AAGCTGPKHS DCLACLHFNH SGICELHCPA LVTYNTDTFE SMPNPEGRYT FGASCVTACP 310        320        330        340        350        360
 YNYLSTDVGS CTLVCPLHNQ EVTAEDGTQR CEKCSKPCAR VCYGLGMEHL REVRAVTSAN 370        380        390        400        410        420
 IQEFAGCKKI FGSLAFLPES FDGDPASNTA PLQPEQLQVF ETLEEITGYL YISAWPDSLP 430        440        450        460        470        480
 DLSVFQNLQV IRGRILHNGA YSLTLQGLGI SWLGLRSLRE LGSGLALIHH NTHLCFVHTV 490        500        510        520        530        540
 PWDQLFRNPH QALLHTANRP EDECVGEGLA CHQLCARGHC WGPGPTQCVN CSQFLRGQEC 550        560        570        580        590        600
 VEECRVLQGL PREYVNARHC LPCHPECQPQ NGSVTCFGPE ADQCVACAHY KDPPFCVARC 610        620        630        640        650        660
 PSGVKPDLSY MPIWKFPDEE GACQPCPINC THSCVDLDDK GCPAEQRASP LTSIISAVVG 670        680        690        700        710        720
 ILLVVVLGVV FGILIKRRQQ KIRKYTMRRL LQETELVEPL TPSGAMPNQA QMRILKETEL 730        740        750        760        770        780
 RKVKVLGSGA FGTVYKGIWI PDGENVKIPV AIKVLRENTS PKANKEILDE AYVMAGVGSP 790        800        810        820        830        840
 YVSRLLGICL TSTVQLVTQL MPYGCLLDHV RENRGRLGSQ DLLNWCMQIA KGMSYLEDVR 850        860        870        880        890        900
 LVHRDLAARN VLVKSPNHVK ITDFGLARLL DIDETEYHAD GGKVPIKWMA LESILRRRFT 910        920        930        940        950        960
 HQSDVWSYGV TVWELMTFGA KPYDGIPARE IPDLLEKGER LPQPPICTID VYMIMVKCWM 970        980        990       1000       1010       1020
 IDSECRPRFR ELVSEFSRMA RDPQRFVVIQ NEDLGPASPL DSTFYRSLLE DDDMGDLVDA 1030       1040       1050       1060       1070       1080
 EEYLVPQQGF FCPDPAPGAG GMVHHRHRSS STRSGGGDLT LGLEPSEEEA PRSPLAPSEG 1090       1100       1110       1120       1130       1140
 AGSDVFDGDL GMGAAKGLQS LPTHDPSPLQ RYSEDPTVPL PSETDGYVAP LTCSPQPEYV 1150       1160       1170       1180       1190       1200
 NQPDVRPQPP SPREGPLPAA RPAGATLERP KTLSPGKNGV VKDVFAFGGA VENPEYLTPQ
```

FIG. 8

P05111 (INHA_HUMAN)

```
        10         20         30         40         50         60
MVLHLLLFLL LTPQGGHSCQ GLELARELVL AKVRALFLDA LGPPAVTREG GDPGVRRLPR 70         80         90        100        110        120
RHALGGFTHR GSEPEEEDV  SQAILFPATD ASCEDKSAAR GLAQEAEEGL FRYMFRPSQH 130        140        150        160        170        180
TRSRQVTSAQ LWFHTGLDRQ GTAASNSSEP LLGLLALSPG GPVAVPMSLG HAPPHWAVLH 190        200        210        220        230        240
LATSALSLLT HPVLVLLLRC PLCTCSARPE ATPFLVAHTR TRPPSGGERA RRSTPLMSWP 250        260        270        280        290        300
WSPSALRLLQ RPPEEPAAHA NCHRVALNIS FQELGWERWI VYPPSFIFHY CHGGCGLHIP 310        320        330        340        350        360
PNLSLPVPGA PPTPAQPYSL LPGAQPCCAA LPGTMRPLHV RTTSDGGYSF KYETVPNLLT

QHCACI
```

METHOD FOR DETERMINING THE RISK OF DEVELOPING BRAIN METASTASIS, AND A KIT TO CARRY OUT SAID METHOD

RELATED APPLICATIONS

This application is a §371 national stage of PCT International Application No. PCT/EP2010/057947, filed Jun. 8, 2010, claiming priority of Spanish Patent Application No. ES 200930294, filed Jun. 10, 2009, the contents of each of which are hereby incorporated by reference into this application.

REFERENCE TO SEQUENCE LISTING

This application incorporates-by-reference nucleotide and/or amino acid sequences which are present in the file named "111209_0206_83572_Substitute_Sequence_Listing_SK .txt," which is 26.6 kilobytes in size, and which was created Dec. 9, 2011 in the IBM-PC machine format, having an operating system compatibility with MS-Windows, which is contained in the text file filed Dec. 9, 2011 as part of this application.

The present invention relates to markers indicative of brain metastasis. These markers find use in determining the risk of developing of metastasis, in particular brain metastasis.

BACKGROUND ART

Cancer is a multistep process and occurs as a result of the loss of control of cell division, leading to initial tumour formation, which can then spread and develop a tumor in a distant organ or metastasis.

A distinguishing feature of malignant cells is their ability to invade surrounding normal tissue, metastasize through the blood and lymphatic systems and re-establish at distant secondary locations. To form metastases, individual tumour cells must break from the primary tumor mass, degrade extracellular matrix, invade the surrounding normal tissue, enter the blood or lymphatic circulation, exit the circulation at a distal tissue and establish satellite colonies within this new tissue environment. This behavior requires the cooperative function of numerous proteins. This metastatic spread of solid tumour is responsible directly or indirectly for most cancer-related deaths.

Clinical management of cancer can be aided by prognosis markers and by therapeutic predictive markers. Prognosis markers assess risk of the disease progression independent of therapy. Therapeutic predictive markers indicate sensibility or resistance of a cancer to a specific treatment. For most cancers and cancer treatments, there exist subsets of patients that will respond to a particular treatment and subsets of patients that will fail to respond to the treatment.

The use of therapeutic predictive markers to identify subsets of patients likely to respond to treatment would facilitate the selection of the appropriate treatment and avoid unnecessary delays associated with ineffective treatment. Additionally, because most cancer treatments are associated with adverse side effects inherent to the treatment, said predictive markers eliminate unnecessary risks of adverse side effects by reducing the administration of cancer treatments to individuals for whom treatment is likely to fail.

Currently, the only recommended therapeutic predictive markers in oncology are ER (estrogen receptor) and PR (progesterone receptor) status for selecting hormone sensitive breast cancers, and HERB-2 for identifying breast cancer patients who may benefit from trastuzumab treatment.

The incidence of brain metastasis in patients with breast cancer overexpressing HERB-2 treated with tratuzumab is twice that in other breast cancer patients. On the other hand, one-third of the patients with breast cancer will develop CNS metastasis and this often occurs when they are responding to therapy at other sites or have a stable disease. Thus, drugs with a high impact on the clinical outcome of metastatic breast cancer patients, such as taxanes or trastuzumab, play only a limited role in the treatment of brain metastasis (Tosoni A. et al., "Chemotherapy in breast cancer patients with brain metastases: Have new chemotherapic agents changed the clinical outcome?", Crit. Rev. Oncol. Hematol. 2008, vol. 68(3), p. 212-221). The resistance to HERB2-target agents remains a substantial clinical problem as many HERB2-positive cancers exhibit intrinsic resistance.

Cerebral metastases occur in 10-15% of breast cancer patients with advanced disease and have recently become a significant clinical problem. It can be assumed that up to 30% of metastatic breast cancer patients will experience brain metastasis during the course of their disease. The increase in this rate could be linked to greater survival in patients receiving chemotherapy and the fact that it is difficult to overcome the blood brain barrier (BBB) with current systemic treatments. The difficulties in managing brain metastasis therapy result in a median survival of seven months, with brain metastasis being the cause of death or a major contributing factor of it in 68% of patients.

An adequate estimation of independent predictive factors at initial tumor diagnosis is required to enable the clinician to determine whether said tumor can metastasize. This information would be useful for the clinician in order to decide between aggressive treatments, to avoid unnecessary treatment, and to design therapies specifically addressed against differential aspects of each metastatic location.

Therefore, there is the need of predictive markers which provides information about the risk of metastasizing a primary tumor to other organs in order to treat efficiently the illness.

SUMMARY OF THE INVENTION

Until now, little was known about predictive factors enabling the early identification of primary cancer patients at risk of central nervous system ("CNS") metastasis. Analysis of metastatic tissues, the use of bioinformatic approaches and the characterization of protein expression in tumors with site-specific metastasis have afforded to the inventors of the present application to find markers which provide specific information about whether cancer cells have a predisposition to metastasize.

Thus, in a first aspect the present invention provides a method for determining the risk of developing brain metastasis in a subject diagnosed with a breast tumour, the method comprising: (a) isolating a sample from the breast tumour; (b) determining the level of expression of GRP94, FN14 or both in the sample, and (c) comparing said level with the level of said gene(s) in a control sample, wherein if it is detected an overexpression of said gene(s), in respect of the control sample, it is indicative of the risk for developing brain metastasis.

As it is shown below, the inventors of the present application have analyzed in depth the pathogenic pathways operating in brain metastasis by protein expression analysis of tissues from metastatic human brain and primary breast tumors, along with further functional analysis of cells. In this way, it has been identified an endoplasmic reticulum stress resistance phenotype (hereinafter also referred as "ERSRP") in breast cancers, which predicts brain metastasis progression and which, at the same time, is useful for therapeutic decision-making. Without being bound to the theory, it is believed that said ERSRP is mainly based on the level of expression of GRP94 and/or FN14.

Surprisingly, the inventors of the present application have found that GRP94 and FN14 are differentially expressed (i.e. are overexpressed) in primary breast tumor samples derived from patients already diagnosed with brain metastasis. In fact, the expression profile of these genes in the primary breast tumor samples derived from these patients was the same than the one found after analyzing brain metastasis samples. These findings support the use of these genes as predictive brain metastasis markers in primary breast tumors.

The differential expression of GRP94 and/or FN14 can confer to the method a greater sensibility, improving the discrimination ability (mainly because the non-detection of GRP94 and/or FN14 will be indicative of no risk of brain metastasis) and, in this way, reducing the false-negatives associated to other diagnostic methods based on the detection of other markers such as HERB-2 (see data shown in Table 2).

As described above, metastasis is a complex process. This complexity makes unpredictable whether a primary tumor can metastasize and which organ(s) can be affected by the metastasis. In this respect, the clinician has the additional problem that metastasis is detected in an advanced stage since the first stages are "silent", so when detected, by imaging techniques, it is very difficult to treat efficiently the patient.

According to the method of the first aspect of the invention, if the clinician, after analysing the breast cancer sample, determines the overexpression of one or both GRP94 and FN14, then additional imaging analysis, for instance NMR, of the brain can be performed to confirm whether the brain metastasis has occurred or not. To the clinician this is of relevance because it would allow him to establish the appropriate protocol to the patient, determining which treatment can be the most effective in order to treat/prevent the illness: if the imaging analysis reveals brain metastasis, the clinician will design a specific treatment, with the advantage that it will have been diagnosed in an early stage; If not, the clinician can establish a protocol to check the patient periodically with a NMR for early diagnosis of brain metastasis and give to the patient a preventive treatment. This means a great advance in the field of cancer because the brain metastasis predisposition can be predicted in an early state, which can lead to a reduction of the final incidence of breast cancer brain metastasis and indeed increase survival.

In a second aspect the present invention provides a kit to carry out the method as defined in the first aspect of the invention, the kit comprising appropriate means to determine the level of expression of each one of the genes. Throughout the description and claims the word "comprise" and variations of the word, such as "comprising", is not intended to exclude other technical features, additives, components, or steps. Additional objects, advantages and features of the invention will become apparent to those skilled in the art upon examination of the description or may be learned by practice of the invention.

The following examples and drawings are provided by way of illustration, and are not intended to be limiting of the present invention.

BRIEF DESCRIPTION OF THE DRAWINGS

FIG. 4 shows the amino acid sequence of GRP94 available in the Swiss Prot database with the ID number P14625 (SEQ ID NO: 1).

FIG. 5 shows the amino acid sequence of FN14 available in the Swiss Prot database with the ID number Q9NP84 (SEQ ID NO: 2).

FIG. 6 shows the amino acid sequence of TRAE2 available in the Swiss Prot database with the ID number Q96NT2 (SEQ ID NO: 3).

FIG. 7 shows the amino acid sequence of HERB2 available in the Swiss Prot database with the ID number P04626 (SEQ ID NO: 4).

FIG. 8 shows the amino acid sequence of Inhibin available in the Swiss Prot database with the ID number P05111 (SEQ ID NO: 5).

DETAILED DESCRIPTION OF PARTICULAR EMBODIMENTS

Figure 1:
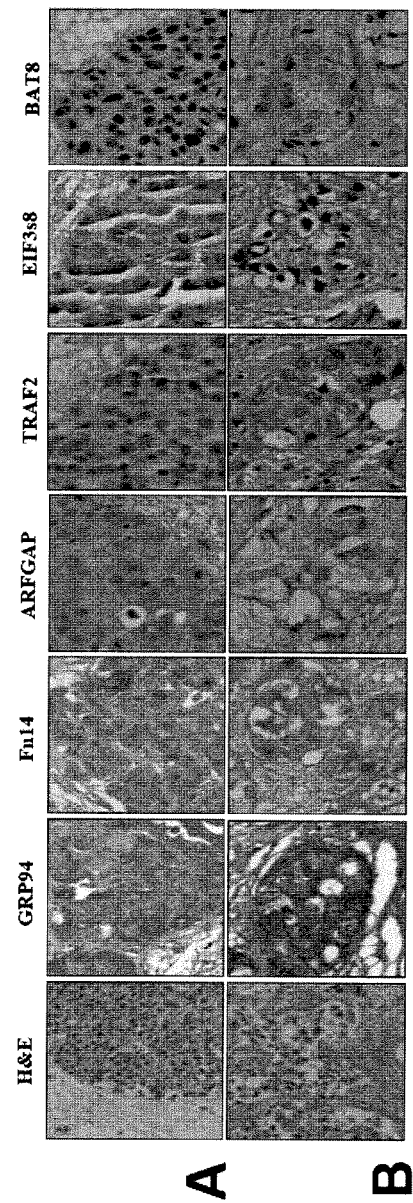
FIG. 1 represents the immunohistochemical analysis to identify the indicated proteins in paraffin-embedded tumor-brain metastasis pairs (×20). Hematoxylin-eosin staining (H & E) of each tissue is shown as viewed by light microscopy (×10). A: Metastasis, B: primary tumor.

The present invention provides a method for determining the risk of developing brain metastasis in a subject diagnosed with a primary breast tumor, the method comprising (a) isolating a sample from the breast tumour; (b) determining the level of expression of GRP94, FN14 or both in the sample, and (c) comparing said level with the level of said gene(s) in a control sample, wherein if it is detected an overexpression of said gene(s), in respect of the control sample, it is indicative of the risk for developing brain metastasis.

The control sample is selected depending on the technique, tools and manufacturer's instructions used in order to determine the level of expression of GRP94 and FN14. For instance, if it is desired to determine the level of GRP94 and FN14 proteins, the skilled in the art would look for appropriate commercially available antibodies and would follow the recommendations of the manufacturer to obtain the best results. An illustrative, non-limitative example is provided in Table 1 below, wherein for each one of the commercial antibodies used for the detection of the target proteins, a specific control tissue is used. Alternatively, the clinician would be able to use a primary breast cancer sample from a patient already diagnosed of brain metastasis as a control to determine whether there is overexpression or not in sample under analysis.

In one embodiment of the first aspect of the invention, it is determined the level of expression of GRP94.

GRP94 (also known as HSP90B1, and having the Swiss Prot ID number P14625) is an endoplasmic reticulum protein from HSP90 protein family protein with a length of 803 aminoacids and with molecular weight 92,469 Da. GRP94 is involved in the conformational maturation of proteins destined for cell-surface display or export. The findings of the inventors of the present application suggest that GRP94 may participate in ERSRP activating PERK, ATF6 and IRE1. Thus, GRP94 overexpression in brain metastasis may be a hinge orchestrating an ERSRP.

In another embodiment of the first aspect of the invention, it is determined the level of expression of FN14.

FN14 (also so-called fibroblast growth factor-inducible 14, and having the Swiss prot. ID number Q9NP84) is a member of the tumor necrosis factor (TNF) superfamily of receptors with a sequence length of 129 AA and molecular weight 13,911 Da. FN14 is an immediate early response gene whose expression is directly activated after exposure to growth factors in fibroblasts and is upregulated in migration-stimulated glioma cells in vitro and it has been related with high-grade tumors.

In one embodiment of the first aspect of the invention, the level of expression of GRP94 and FN14 is determined.

As shown the results of Table 3, GRP94 is the most sensitive in HERB2 positive tumors, whereas FN14 is the most specific in HERB2 negative tumors. The combined detection of both markers confers to the method of the present invention a reliable prediction of the risk that a primary breast tumor can metastasize to the brain.

In another embodiment of the first aspect of the invention, the method further comprises determining the level of expression of TRAF-2. It has been found that TRAF-2 is overexpressed in breast cancer brain metastasis, and that it shows a sensibility value higher than the one shown by HERB2 (see Table 2). Thus, the combination of GRP94 and/or FN14 together with TRAF2 improves the sensibility of the method of the present invention.

As shown below, when the positive and negative likelihood were calculated in order to assess the predictive accuracy of each of the three genes (i.e., GRP94, TRAF2 and FN14) as a brain metastasis marker, GRP94 was the best negative predictive marker, followed by TRAF2 and FN14. In fact, it was found that the predictive accuracy of these markers was better than the one for HERB2. Thus, the absence or the insignificant detection of at least one of these markers in tumors accurately predicts the absence of brain metastasis. TRAF2 (also so-called "NF receptor-associated factor 2" and having the Swiss protein ID number Q96NT2) is a member of the TNF receptor associated factor (TRAF) protein family with 501 AA length and molecular weigth 55,859 Da. TRAF proteins mediate the signal transduction from members of the TNF receptor superfamily. This protein directly interacts with TNF receptors, and forms a heterodimeric complex with TRAF1.

In one embodiment of the first aspect of the invention, the method further comprises determining the level of expression of HERB2.

HERB2 is also commonly referred to as Her-2/neu (Swiss protein ID number P04626) with 1,255 AA length and molecular weigth 137,910 Da. This gene is one member of a family of genes that provide instructions for producing growth factor receptors.

In another embodiment of the first aspect of the invention, the method further comprises determining the level of expression of Inhibin.

Inhibin (Swiss prot ID number P05111) is a peptide that is an inhibitor of FSH synthesis and secretion, and participates in the regulation of the menstrual cycle. Inhibin has 366 AA length and molecular weigth of 39,670 Da.

It has been found that Inhibin is not significantly expressed in breast cancer samples derived from patients already diagnosed with brain metastasis. Therefore, when this marker is not detected or (not significantly detected) in the sample, it will be indicative of predisposition to develop brain metastasis. When this marker is used as brain metastasis marker, it confers to the method of the invention a specificity higher than 80%. Therefore, if the method of the invention comprises determining the level of expression of GRP94 and/or FN14 and Inhibin, the method will gain accuracy in the prediction of brain metastasis.

In another embodiment of the first aspect of the invention, the method comprises determining the level of expression of one of the following set of markers: (a) GRP94, FN14, Inhibin; (b) GRP94, TRAF2, HERB2, and FN14; (c) GRP94, FN14, Inhibin and HERB-2; and (d) GRP94, FN14 and TRAF2. When the method is based on the overexpression of GRP94, FN14 and TRAF2 (data not shown), it is achieved a well correlation with brain metastasis in breast cancer patients. The predictive power using the combination of these markers is better than the one achieved with only HERB2 (which is, at the moment, the commonly predictive marker used). The method based on these three gene markers represents a new tool to discriminate the risk of brain metastasis in HERB2 positive and negative breast cancers.

Either GRP94, FN14 and TRAF2 might be useful for therapeutic decision-making, as they could indicate therapy response.

It is believed that ERSRP may predict those patients who could be treated more effectively with compounds different from trastuzumab or even treated to prevent the development of the disease.

Figure 3:
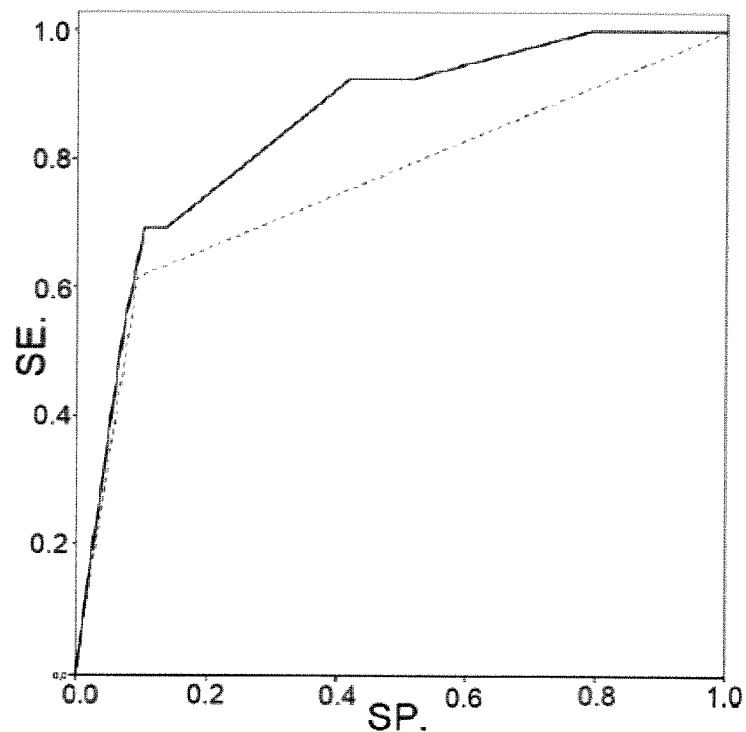
FIG. 3 represents the ROC curve (SE. (sensibility) vs. SP (specificity)) for the HERB2 marker (dotted line) and for the combination GRP94+FN14+Inhibin (continuous line).

Performing a multivariate analysis based on stepwise logistic regression revealed that GRP94, FN14, and Inhibin are the best combination to predict brain metastasis. The area under the ROC curve for this combination was 0.85, while the area under the ROC curve for HERB2 alone was 0.76 (FIG. 3). The combination of markers was a significant improvement over the prediction performance of HERB2.

It was also performed a stratified analysis to check the relationship between HERB2 positivity and ERSRP in binary combinations. It was found that performing the analysis of GRP94, TRAF2 and FN14 expression it was significantly increased the prediction of metastatic disease in brain compared to HERB2 alone.

The kit according to the second aspect of the invention comprises appropriate means to perform the method as defined in the first aspect of the invention. The presence of the markers forming part of the method of the first aspect of the invention can be determined on the basis of the mRNA transcripts or proteins. In this way, the kit according to the second aspect of the present invention will include appropriate means to determine either the presence of mRNA transcripts or the corresponding protein.

Methods and means for determining the amount of mRNA of a particular gene in a sample are well known in the state of the art.

The polymerase chain reaction (PCR) is the most widely used method for the in vitro enzymatic amplification of nucleic acids, but it is not the only one. The ligase chain reaction (LCR), for example, can be used for the sensible detection of a DNA sequence with an increased specificity as compared to PCR (LCR can be used for the discrimination among alleles). During LCR, for each of the two DNA strands, two partial probes are ligated to form the actual one; thus, LCR uses two enzymes: a DNA polymerase and a DNA ligase. Each cycle results in a doubling of the target nucleic acid molecule.

A quantitative method for the determination of nucleic acids is real time PCR. Real time PCR, also called quantitative real time PCR (qPCR), is used to amplify and simultaneously quantify a targeted DNA molecule. The procedure follows the general principle of polymerase chain reaction; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce when hybridized with a complementary DNA.

Further strategies have been developed based on the original PCR for the amplification of RNA, such as reverse transcription polymerase chain reaction (RT-PCR). In this technique, the RNA strand is first reverse transcribed into its DNA complement or complementary DNA, followed by amplification of the resulting DNA using polymerase chain reaction. Another method in molecular biology which is used to amplify RNA sequences is Nucleic Acid Sequence Based Amplification (NASBA). Explained briefly, NASBA works as follows: (a) RNA template is given to the reaction mixture and the first primer attaches to its complementary site at the 3' end of the template; (b) Reverse transcriptase synthesizes the opposite, complementary DNA strand; (c) RNAse H destroys the RNA template (RNAse H only destroys RNA in RNA-DNA hybrids, but not single-stranded RNA); (d) the second primer attaches to the 5' end of the DNA strand and 5-T7 RNA polymerase produces a complementary RNA strand which can be used again in step (a). NASBA has been introduced into medical diagnostics, where it has been shown to give quicker results than PCR, and it can also be more sensitive. Both RT-PCR and NASBA are both suitable techniques for the determination of gene expression. Preferably, the level of expression of the genes is determined by RT-PCR.

Other suitable techniques for the determination of gene expression are macroarray screening, microarray screening, and nanoarray screening.

There are well known in the state of the art several methods for determining the amount of a protein in a sample. Generally, these methods will make use of binding moieties, which are molecules or molecule segments capable of binding specifically to the target protein (in the present case the target protein is the protein encoded by the gene from which its expression is determined). Polypeptide binding moieties can be identified by means of a screen. A suitable method or screen for identifying peptides or other molecules which selectively bind a target protein may comprise contacting the target protein with a test peptide or other molecule under conditions where binding can occur, and then determining if the test molecule or peptide has bound the target protein or peptide. Methods of detecting binding between two moieties are well known in the art of biochemistry.

Preferably the binding moiety can be a polypeptide molecule (such as an antibody or a fragment thereof) or a nucleic acid aptamer, among others. The most frequently used binding molecules are antibodies.

By "antibody" is meant a whole antibody, including without limitation a chimeric, recombinant, transgenic, humanised, grafted and single chain antibody, and the like, or any fusion protein, conjugates, fragments, or derivates thereof that contain one or more domains that selectively bind the target protein or peptide. "Antibody" therefore includes a whole immunoglobulin molecule, a monoclonal antibody, a chimaeric antibody, a humanised antibody, a human antibody, or an immunologically effective fragment of any of these. An antibody fragment means an Fv, a disulfide linked Fv, scFv, Fab, Fab', or F(ab')2 fragment, which are well known in the art, or any part of the antibody with adequate size and conformation to bind to the target protein or peptide. There are various advantages for using antibody fragments, rather than whole antibodies.

Monoclonal antibodies (MAbs) are mono-specific antibodies. Given (almost) any substance, it is possible to create monoclonal antibodies that specifically bind to that substance. MAbs can be produced by techniques that are well known in the state of the art.

Antibodies are frequently employed for the determination of the expression of a particular protein within a cell by immunohistochemical or immunofluorescent techniques. Preferably, the technique to be used in the present invention is inmunohistochemistry (IHC). IHC is a well known technique that is widely used to understand the distribution and localization of biomarkers and differentially expressed proteins in different parts of a biological tissue.

EXAMPLES

Materials and Methods

Human Brain Metastasis Cells and Tissues

MDA-MB 435 cell cultures (435-P) and 435-Br1 cells, are well-characterized human models (given by Àngels Fabra from IDIBELL), established from brain metastasis in nude mice with the ability to metastasize to the brain (Schackert G. et al., "Unique patterns of brain metastasis produced by different human carcinomas in athymic nude mice", *Int. J. Cancer,* 1989, vol. 44, vol. 892-897; Zhang R. D. et al., "Relative malignant potential of human breast carcinoma cell lines established from pleural effusions and a brain metastasis", *Invasion Metastasis,* 1991, vol. 11, p. 204-215). These cell cultures were maintained in 1:1 (v/v) mixture of Dulbecco's modified Eagle's medium and Ham's F12 medium supplemented with 10% fetal bovine serum, 1 mmol/L piruvate, and 2 mmol/L L-glutamine in 5% $CO_2$-95% air at 37° C. in a humidified incubator.

For functional studies it was also used other metastatic variants derived from primary cultures of liver (435-Liver) and lung (435-Lung) metastasis (Martin B. et al., "Functional Clustering of Metastasis Proteins Describes Plastic Adaptation Resources of Breast-Cancer Cells to New Microenvironments", *J. Proteome Res.,* 2008, vol. 7, p. 3242-3253). In some experiments bone metastatic cells from MDA-MB 231, BO2 cells provided by P. Clézardin (IN-SERM U.664, Faculté de Médecine Laennec, Lyon, France), were used.

To confirm protein expression there were used six brain metastases matched with the corresponding ductal breast carcinoma from patients surgically treated at the Hospital Universitari de Bellvitge, HUB.

It was also used primary ductal breast carcinomas at initial diagnosis to assess the predictive value of each protein. The Breast Cancer Committee of the Catalan Institute of Oncology (I.C.O.) and the HUB supplied samples from patients diagnosed between 1988 and 2006. The series included 71 consecutive tumors at initial diagnosis from metastatic patients, with one or several organs affected and 51 patients with positive lymph nodes at surgery without metastatic progression after a minimum follow-up of five years. To optimize each immunohistochemical analysis, control tissues of breast cancer (GRP94, TRAF2), testis (inhibin), kidney and heart (FN14) were also used (See Table 1 below).

Identification of Cancer Candidates

The procedure for identifying novel cancer candidates has been described by Aragues and colleagues (Aragues R. et al., "Predicting cancer involvement of genes from heterogeneous data", BMC Bioinformatics, 2008, vol. 9, p. 172). In a first step, a protein-protein interaction network ("PPIN") was built from a target set of proteins known to be involved in cancer (i.e., seed proteins). Then, gene expression levels were mapped onto the network proteins. A protein is considered to be differentially expressed if the gene encoding for it was found differentially expressed in the microarray experiment. Finally, a list of candidate cancer genes was produced.

To classify proteins by their function we used FatiGo software; a web tool for detecting significant associations between gene ontology terms and groups of genes (Al-Shahrour F. et al., "FatiGO: a web tool for finding significant associations of Gene Ontology terms with groups of genes", Bioinformatics, 2004, vol. 20, p. 578-580).

Experimental Proteomic Analysis and Protein Interaction Network Analysis

It was used prior proteomic analysis which compared differential expression of proteins between 435-P and 435-Br1 cells, to create and analyze a protein-protein interaction network (Martin B. et al., "Biological pathways contributing to organ-specific phenotype of brain metastatic cells", J. Proteome Res., vol. 7, p. 908-920.). Briefly, the proteins differentially expressed by two-dimensional gel electrophoresis (Ettan™ DIGE, Amersham Biosciences AB) in 435-Br1 cells were identified by peptide mass fingerprinting spectra recorded by a Voyager STIR MALDI-TOF (Applied Biosystems) in positive reflector mode with delayed extraction. The spectra were analyzed using the m/z program (Proteometrics, New York, N.Y.). Proteins were identified against a non-redundant database (NCBI) using the MASCOT program (http://www.matrixscience.com).

The protein network was based on 17 known proteins. We used PIANA (Aragues R. et al., "PIANA: protein interactions and network analysis", Bioinformatics, 2006, vol. 22, p. 1015-1017) to combine data from DIP 2006.01.16, (Salwinski L. et al., "The Database of Interacting Proteins: 2004 update", Nucleic Acids Res, 2004, vol. 32, p. D449-451) MIPS 2006.01 (Pagel P. et al., "The MIPS mammalian protein-protein interaction database", Bioinformatics, 2005, vol. 21, p. 832-834), HPRD 2005.09.13 (Peri S. et al., "Human protein reference database as a discovery resource for proteomics", Nucleic Acids Res., 2004, vol. 32, p. D497-501), BIND 2006.01 (Alfarano C. et al., "The Biomolecular Interaction Network Database and related tools 2005 update", Nucleic Acids Res., 2005, vol. 33, p. D418-424) and the human interactions from two high-throughput experiments (Rual J. F. et al., "Towards a proteome-scale map of the human protein-protein interaction network", Nature, 2005, vol. 437, p. 1173-1178; Stelzl U. et al., "A human protein-protein interaction network: a resource for annotating the proteome", Cell, 2005, vol. 122, p. 957-968).

The integration of many different sources of interactions into a single repository allowed working with an extensive set of 363,571 interactions between 42,040 different protein sequences. The initial set of proteins was referred to as "seed proteins". In this network, a protein that was connected to more than one seed was referred to as a N-linker, N being the number of seed proteins to which it is connected:

Finally, proteins only connected to one seed protein were called leaves (Dawelbait G. et al., "Structural templates predict novel protein interactions and targets from pancreas tumour gene expression data", Bioinformatics, 2007, vol. 23, p. i115-124; Cockell S. J. et al., "Structure-based evaluation of in silico predictions of protein-protein interactions using Comparative Docking", Bioinformatics, 2007, vol. 23, p. 573-581).

Human Brain Metastasis Transcriptomic Data

It was used the list of differentially expressed genes for 4 brain metastases from breast cancer patients obtained from the MetaBre Consortium. They were analyzed by microarray hybridization using the GeneChip Human Genome U133 Plus 2.0 Array (Affymetrix, UK Ltd, UK), which includes over 47,000 transcripts and variants, following standard protocols for RNA extraction and probe preparation (Landemaine T. et al., "A six-gene signature predicting breast cancer lung metastasis", Cancer Res., vol. 68, p. 6092-6099). To process and normalize Affymetrix chips, Robust Multichip Averaging (RMA) algorithms were used (Irizarry R. A. et al., "Exploration, normalization, and summaries of high density oligonucleotide array probe level data", Biostatistics, 2003, vol. 4, p. 249-264). All these computations were performed with the Bioconductor package (Gentleman R. C. et al., "Bioconductor: open software development for computational biology and bioinformatics", Genome Biol., 2004, vol. 5, p.R80). Expression profiles were analyzed with BRB Array tools, version 3.3beta3 (Biometric Research Branch, Division of Cancer Treatment and Diagnosis Molecular Statistics and Bioinformatics Section, National Cancer Institute, Bethesda, Md., U.S.A.). Two different procedures were used for comparisons: (1) the fold change for each gene in brain metastasis, compared to a pool of primary breast carcinomas (Lonnstedt I. et al., "Replicated microarray data", Statistica Sinica, 2002, vol. 12, p. 31-46); (2) and an univariate t-test (Landemaine T. et al., "A six-gene signature predicting breast cancer lung metastasis", Cancer Res., vol. 68, p. 6092-6099) to identify genes differentially expressed in brain metastasis and metastasis in organs other than the brain (5 lung, 6 liver, 2 skin, and 6 osteolytic bone metastasis samples).

The list obtained in the same experiments of differentially expressed genes in metastases other than brain metastasis (lung, liver and bone genes) with regard to a pool of breast cancer tumors was also used for comparisons.

Tissue Microarrays (TMAs) and Immunohistochemistry

TMAs were prepared from three representative areas of the tumor which were carefully selected from hematoxylin-eosin-stained sections of a 122-donor blocks. Core cylinders of 0.6 mm diameter were punched from each of them with a skin-biopsy punch and deposited into recipient paraffin blocks using a specific arraying device (Beecher Instruments, Sun Prairie, Wis.) as described in Fernandez and colleagues (Fernandez P. L., et al., "Tissue macroarrays ("microchops") for gene expression analysis", Virchows Arch., 2001, vol. 438, p. 591-594). In addition to tumors, the recipient block also contained 6 normal breast samples. Three-µm sections of the resulting microarray block were made and used for IHC analysis after being transferred to glass slides.

The experimental conditions, the characteristics, and source of the antibodies used are listed in Table 1.

TABLE 1

| IHC VALIDATION | Antibody | Clone & Company | Protocols | Cellular expression | Control Tissue |
|---|---|---|---|---|---|
| BRAIN PROTEOMICS | GRP 94 | sc-1794 (C-19) (Santa Cruz Biotechnology, Santa Cruz, CA) | 1/2000 (retrieved in Na-citrate buffer) | Endoplasmic reticulum | Breast carcinoma |
| | TRAF2 | SM7106P (clon 33A1293; 205-222 aa) (Acris, Acris Antibodies GmbH, Germany) | 1/100 o/n (retrieved in Na-citrate buffer) | Cytoplasm | Breast carcinoma |
| | FN14 | SC-27143 (C-13) (Santa Cruz Biotechnology) | 1/3000 (retrieved in Na-citrate buffer) | Membrane | Kidney/heart |
| BRAIN MetaBre SIGNATURE | INHA | MCA951ST (R1) (abD serotec; a Division of Morphosys, Germany) | 1/50 (retrieved in Na-citrate buffer) | Cytoplasm | Testis |
| | TOP1 | ab3825 (401-600 aa) (Abcam; Abcam plc, UK) | 1/100 (retrieved in TRIS/EDTA) | Nuclei/cytoplasm | Colorectal tumor |
| | VAV2 | sc-20803 (H-200) (Santa Cruz Biotechnology) | 1/1000 (retrieved in Na-citrate buffer) | Cytoplasm | Pancreas |
| OTHER VALIDATIONS | GFAP | Z0334 (Dakocytomation, Dako Diagnostics S.A, Denmark) | 1/8000 (retrieved in Na-citrate buffer) | Cytoplasm | Brain (astrocytes) |
| | TEM 8 | ab21270 (Abcam) | 1/2000 (retrieved in Na-citrate buffer) | Cytoplasm/membrane | Brain Tumor endothelium |
| | ARFGAP | SP1402P (Acris) | 1/1000 (retrieved in Na-citrate buffer) | Cytoplasm | Testis |
| | EIF3s8 | ab19359 (N-terminal 1-50 aa) (Abcam) | 1/1000 o/n (retrieved in Na-citrate buffer) | Cytoplasm | Kidney |
| | BAT 8 | G-6919 (Sigma-Aldrich, st. Louis, MO) | 1/250 (retrieved in Na-citrate buffer) | Cytoplasm | Lymph node |

Positive control tissues for each protein were used as a reference for TMA staining intensity.

Antigens were retrieved by heating in a pressure cooker for 20 minutes in the appropriate buffer (as indicated in Table 1, above). Primary antibodies were diluted in Dako Real™ Antibody Diluent Buffer (Dakocytomation): Tris buffer, ph 7.2, 15 mM $NaN_3$. LSAB+System-HRP (Dakocytomation) was used, including the biotinylated anti-rabbit, anti-mouse and anti-goat immunoglobulins in PBS; streptavidin conjugated to HRP in PBS; and liquid 3-3' diaminobenzidine in chromogen solution. The polyclonal antibody anti-HERB2, A0485 (DAKO) was used with the Ultraview detection kit in automatic staining system (Benchmark XT, USA).

Immunoreactivities were classified by estimating the percentage of tumor cells showing characteristic staining (from "undetectable" or 0%, to homogeneous staining or 100%) and by estimating the intensity of staining (1, weak or negative staining; 2, moderate staining; or 3, strong staining). The cut-off values were the same for all markers tested: strong staining with more than 50% of expressing cells was considered as positive (FIG. 2) (Ginestier C. et al., "Distinct and complementary information provided by use of tissue and DNA microarrays in the study of breast tumor markers", Am. J. Pathol., vol. 161, p. 1223-1233; Jacquemier J. et al., "Protein expression profiling identifies subclasses of breast cancer and predicts prognosis", Cancer Res., 2005, vol. 65, p. 767-779). Reproducibility of the method was checked by using multiple interpreters and reliability by comparison with standard immunohistochemistry on full sections. Slides were evaluated under a light microscope by two researchers.

Western-Blot Analysis (WB)

Cells from exponential cultures were lysed in 200 RIPA buffer. The separated proteins in 7% or 12% polyacrylamide gel were transferred to PVDF membranes (Immobilon-p, Millipore Corporation, Bedford, Mass.). The following antibodies were used: GRP94, clone C-19 (Santa Cruz) at 1/1000; GRP78, clone N-20 (Santa Cruz) at 1/500; HSP70, clone C92F3A-5 at 1/1000 (Stressgen, Ann Arbor, Mich.); GRP58, product E1031 at 1/200 (Sigma), HSP60, clone LK1 (Abcam) at 1/200; TRAF2, clone 33A1293 at 1/100 (Acris Antibodies, GmbH, Germany); ATF6, clone 70B14B.1 at 1/200 (Acris). Anti-human actin monoclonal antibody 1/2000 (Sigma) and anti-human tubulin α, clone B-5-1-2 (Sigma) at 1/10,000, were also used as internal standards for densitometric analysis, for which a band was measured using the Quantity One program; the quantity of a band is calculated as the sum of the intensities of all the pixels within the band boundary multiplied by the area of each pixel.

Peroxidase conjugated goat anti-rabbit secondary antibody 1/2000 (Amersham), or anti-mouse secondary antibody 1/2000 (Pierce, Perbio Science Ltd., Cheshire, UK) or anti-goat secondary antibody 1/3000 (Santa Cruz) was used as appropriate in each case.

Immunoreactive bands were viewed on a VersaDoc™ (Bio-Rad) Imaging System using the Super Signal west-Pico (Pierce). MWs were established with See Blue Plus2 prestained Stantard (Invitrogen, San Diego, Calif.).

Statistical Analysis

To perform the statistical analysis the suggestions of STARTD (http://www.stard-statement.org/) were followed.

Two-way analysis of variance was used to compare mean expression levels. Immunohistochemistry markers were graded on a three-category scale (negative, weak positive, and strong positive). The predictability of brain metastasis for each marker was tested using a 2-sided Fisher exact test and summarized by calculating the sensibility among tumors that developed metastasis, and specificity among tumors without metastasis, for strong positive values (those having more than 50% of positive cells). Positive and negative likelihood ratios were also calculated as integrated predictive indexes, so was the area under the ROC curve. Markers were assessed using a multivariate logistic regression model in a forward stepwise procedure to identify the best combination to predict brain metastasis. Since HERB2 was already a known metastasis risk factor, an analysis including HERB2 as the baseline was also performed as well as a stratified analysis of each candidate marker within HERB2 positive and negative tumors. In all the analyses, associations were considered significant when $p<0.05$.

Results a) Experimental Protein-Protein Interaction Network (PPIN) Validated with Brain Metastasis Transcriptomics The inventors used an integrated approach to build, test, and refine a model of cellular pathways involved in brain metastasis progression using a PPIN. It was used a previously obtained brain metastasis PPIN (cf. Martin B. et al., "Biological pathways contributing to organ-specific phenotype of brain metastatic cells", J. Proteome Res., 2008, vol. 7, p. 908-920) which included 628 proteins from 13 known seeds identified by MALDI-TOF. 8 proteins were underexpressed in brain metastatic cells with respect to the parental cells (glyoxalase 1, keratin 1, heat shock protein 27 (HSP27) and 70 (HSP70), galectin 1, RAD 50-splice isoform 3, 40s ribosomal protein s12 and cathepsin D) and 5 were overexpressed (34/67 kDa laminin-receptor (34/67-LMR), keratin 10, vimentin, ATP synthase β chain and tubulin β5).

The PPIN was compared with 5,235 differentially expressed brain metastasis genes with regard to a pool of primary breast carcinomas from transcriptomics (fold change, $\geq 2$, or $\leq 2$). Using this method (cf. Lonnstedt I. et al., "Replicated microarray data", Statistica Sinica, 2002, vol. 12, p. 31-46), 556 protein-gene pairs corresponding to 183 different genes, 48 underexpressed and 135 overexpressed (data not shown) were found in the network (29.14% in silica proteins).

To functionally classify this brain protein signature it was used the FatiGO software, which through ID Ensembl looks for GO Terms to arrive at a preponderant function of statistically significant proteins in clusters of co-expression. 112 GO Terms-codes were classified: 34 nucleic acid metabolisms (36.17%), 29 translation proteins (30.85%), 18 protein modifications and foldings (19.15%), 9 cell deaths (9.58%) and a miscellaneous of metabolic transport and signaling proteins (data not shown).

b) Organ-Specific Brain Metastasis Functional Signature

The signature of brain genes was catalogued as the brain-specific metastasis signature (BMOS) with a hierarchical clustering which clearly distinguishes between the different metastases (cf. Landemaine T. et al., "A six-gene signature predicting breast cancer lung metastasis", Cancer Res., 2008, vol. 68, p. 6092-6099). The BMOS contained 1,193 genes (MetaBre) after the one-versus-all (ONA) class comparisons identified genes differentially expressed in the 4 brain metastases as opposed to in the 19 others: 6 bone, 5 lung, 2 skin, and 6 liver.

Integrating genomic and proteomic analyses as described above, the inventors matched the BMOS with the protein network obtained in the previous section and obtained 38 brain-specific proteins: 7 underexpressed and 31 overexpressed. These included 13 nucleic acid metabolism proteins (48.15%), 10 translation proteins (37.04%), 7 cell death proteins (25.93%), 6 modification and folding proteins (22.22%) as well as a miscellany of metabolic, transport and signaling proteins, some of them with several functions. These proteins further classified with the FatiGO software was validated as a functional organ-specific signature with a slight increase in cell death genes).

Moreover, five functions from the PPIN were predominant: DNA binding and repair; protein folding and chaperones, which engage one more DNA binding protein (O14776); structural cytoskeleton, which engages four new DNA binding proteins (Q9POW2, P33991, Q53X93, Q9UJN0), two new signal transduction factors (P50453, P16220), one ubiquitinization protein (Q96BH1), one amino acid metabolism protein (Q8N6T7), and one protein involved in methylation (Q96KQ7); protein biosynthesis, which engages four new signal transduction factors (P29692, Q96I38, Q8IWK1, P05111); and a vesicle transport protein (Q8N6T3).

The inventors of the present application searched for references to brain metastasis signatures in published genomic data from experimental and clinical breast cancer and metastasis analysis, but found none. From the list of genes, only seven appeared in previous lists of gene expression profiling predicting clinical outcomes of breast cancer: EEF1 D, MCM4, RPL5, RPS12 and CLN3, from gene expression profiling which predicts clinical outcome (cf. van 't Veer et al., "Gene expression profiling predicts clinical outcome of breast cancer", Nature, 2002, vol. 415, p. 530-536) and FAM3A and TBCD from the gene expression signatures in breast cancer outcome prediction (cf. Nevins J. R. et al., "Towards integrated clinico-genomic models for personalized medicine: combining gene expression signatures and clinical factors in breast cancer outcomes prediction", Hum. Mol. Genet., 2003, vol. 12 Spec No 2:R153-157). GFAP, ubiquous protein in CNS, appeared also in a list of genes differentially expressed between brain and bone breast cancer metastasis (cf. Klein A. et al., "Identification of brain- and bone-specific breast cancer metastasis genes", 2008, Cancer Lett., (Electronic)).

Additional immunohistochemical experiments were carried out on the six matched breast cancer tumor brain metastasis samples from patients to corroborate the differential expression of some proteins representatives of the functions involve. It was validated the expression of GRP94, protein folding and chaperones, in all pairs (6/6) with a similar cytoplasm staining intensity; FN14, from the tumor necrosis factor receptor family engaged with the protein folding and chaperone node, which had a particular membrane and increased cytoplasm staining in brain metastasis (6/6); and TRAF2, adapter protein and signal transducer that links members of the tumor necrosis factor receptor family to different signaling pathways which displayed clear cytoplasm staining.

To validate the organ-specific character of this signature, the inventors went back to the transcriptomic data to check the expression in metastases other than brain (liver, lung and bone) of genes known to be involved in endoplasmic reticulum stress (ERS) response. The present inventors looked for different functional groups of genes: endoplasmic reticulum chaperones, classical stress sensors, protein folding/unfolding response, classical signaling pathways, oxidative stress resistance, proteasome, glucose transporters, amino acid metabolism groups, protein transporters, and receptors and signal transductors. From these, the most differentially overexpressed were GRP94 protein, 10 fold, in brain metastasis but also in lung, 6.5 fold, and bone, 3.3 fold; HSP90, 22 fold, in brain followed by bone, 7.5 fold; calreticulin, 8 fold, which shows a slight increase in bone and lung. Most specifically, in brain 26S proteasome subunit overexpressed 12 fold, tyrosine-protein kinase HERB2 receptor, 32 fold, and epidermal growth factor receptor, 9.5 fold. In contrast, other functions had no relevant expression in brain, for example glucose metabolism overexpressed only in liver or amino acid metabolism. Therefore, according to the expression of these genes in the four different metastases the inventors hypothesized that brain metastasis has a particular functional phenotype, different from those of other metastases which grow in lung, liver or bone.

Of the proteins validated, those involved in protein folding and chaperones might connect different functions and presumably act by rescuing cells from ERS responses. Indeed, the integrated mechanism involves the unfolded protein responses (UPR) to establish a communication axis between the endoplasmic reticulum (ER) and the nucleus, the ER-associated degradation machinery, the ER export machinery, and an interface with mitochondria involved in the activation of proapoptotic mechanisms. GRP94, the most abundant glycoprotein in ER, is involved in the conformational maturation of proteins destined for cell-surface display or export. GRP94, like BiP, might participate in ERSRP activating PERK, ATF6 and IRE1. Thus, GRP94 overexpression in brain metastasis might be a hinge orchestrating an ERSRP.

Apoptosis can be induced via IRE1 and TRAF2 by release of calcium from ER stores. Moreover, the over-expression of FN14 through TRAF2 signaling, as TNFα receptors, might be a potential mediator of cell survival, since activation induces translocation from the cytoplasm to the nucleus, upregulating anti-apoptotic proteins. Thus, the ability of brain metastatic cells to handle stress may condition their intrinsic capacity to survival and contribute to brain metastasis progression and therapy resistance. Since GRP94 was also an organ-specific brain metastasis molecule in patient samples, the inventors of the present application hypothesized that GRP94 could orchestrate the endoplasmic reticulum stress responses (ERSR), inducing compensatory pathways to inhibit cell death.

c) Expression of ERSRP in Breast Cancer Primary Tumors Predicts Brain Metastasis Progression In order to estimate the probability for specific brain metastasis outcomes, it was analyzed the ERSRP generated in a series of primary breast cancer tumors to determine its value as a putative tool for early prediction at initial diagnosis.

Tissue array technology (TMA) was chosen because it allows the simultaneous analysis of many archived tumor samples arrayed on glass slides by traditional immunohistochemical analysis on paraffin-embedded tissues with a long follow-up. TMA permitted to check the expression of GRP94, TRAF2 and FN14 selected from the proteomic analysis in primary breast tumors. It was also checked VAV2, TOP1 and Inhibin, which scored well as brain organ-specific in the previous transcriptomic data and further validated by IHC at the protein expression level. The results are summarized in Table 2:

TABLE 2

BRAIN METASTASIS MARKERS

|  | Sensibility | Specificity | LR (+) | LR (−) | Fisher's Exact Test (2-sided) |
|---|---|---|---|---|---|
| HERB2 | 8/13 (61.5) | 90/99 (90.9) | 6.70 | 0.42 | <0.0001 |
| GRP94 | 12/13 (92.0) | 55/107 (51.4) | 1.89 | 0.16 | 0.003 |
| FN14 | 9/13 (69.2) | 70/104 (77.0) | 3.01 | 0.40 | 0.001 |
| TRAF2 | 9/11 (81.8) | 45/88 (51.1) | 1.67 | 0.35 | 0.055 |
| VAV2 | 2/13 (15.4) | 95/107 (88.8) | 1.38 | 0.95 | 0.65 |
| TOP1 | 4/13 (30.8) | 91/105 (86.6) | 2.30 | 0.80 | 0.11 |
| Inhibina | 0/13 (0) | 97/107 (90.7) | 0 | 1.10 | 0.60 |

Figure 2:
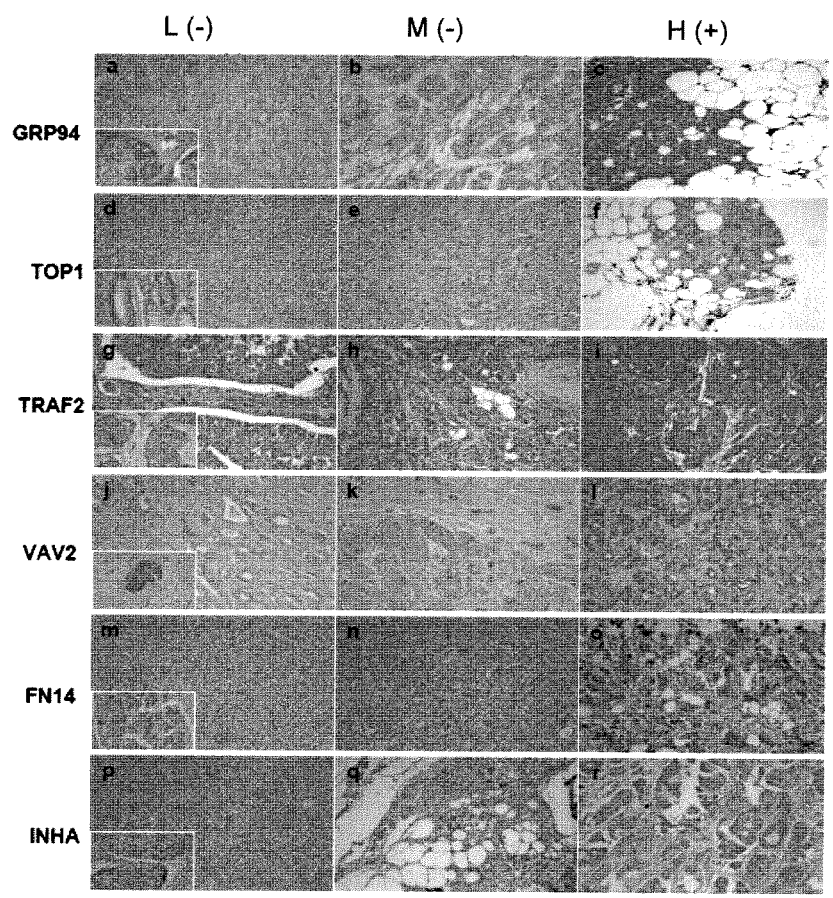
FIG. 2 shows the protein expression in breast cancer tissues for each indicated protein performing immunohistochemistry. Low and medium intensities of staining were considered as negative for semi-quantitative purposes (L(−) and M(−), respectively), and only tumors with high (H) intensity staining were taken into account as positive samples. Small squares are the standard positive control tissue sample used in each determination.

Expression was previously optimized and scored for the six pairs of matched breast cancer tumors and brain metastases (FIG. 1). As expected, staining for all antibodies was homogeneous with different intensities among them. It was considered a marker to be positive when high expression was detected, to avoid unnecessary false positives, taking into account the known expression in a control tissue (FIG. 2).

Statistical analysis of the data showed significant associations between brain metastasis progression and high expression of GRP94 ($p<0.0001$), TRAF2 ($p<0.001$), FN14 ($p<0.0001$), TOP1 ($p=0.032$), and VAV2 ($p=0.005$). Inhibin expression was not associated with brain metastasis progression ($p=0.2$). As expected, HERB2 expression was associated with brain metastasis with a high significance ($p<0.0001$); as well as with the absence of hormone receptors, ER: 54.6% versus 29.6% (6/11 and 29/98, respectively, $p=0.016$) and PR: 72.7% versus 39.0% (8/11 versus 37/95, respectively, $p=0.009$). A slight association with the histological grade (HG) was also observed, HG III 46.9% (7/12 versus 45/96, $p=0.105$).

It was calculated the positive and negative likelihood ratios to assess the predictive accuracy of each molecule as a brain metastasis marker, considering the sensibility and the specificity of each. The highest predictive value for the presence of the metastatic disease was HERB2 expression (positive LR 6.7, $p<0.0001$), followed by FN14 (positive LR 3.01, $p<0.001$), GRP94 (positive LR 1.89 $p<0.003$) and TRAF2 (positive LR 1.67, $p<0.055$). Furthermore GRP94 was the best negative predictive marker (negative LR 0.16), followed by TRAF2 (negative LR 0.35), FN14 (negative LR 0.40) and HERB2 (negative LR 0.42). Thus, the absence of ERSRP in tumors predicted the absence of brain metastasis.

A multivariate analysis based on stepwise logistic regression retained GRP94, FN 14 and Inhibin as the best combination to predict brain metastasis. The area under the ROC curve for this combination was 0.85 (95% Cl 0.75-0.96) while the area under the ROC curve for HERB2 alone was 0.76 (95% Cl 0.58-0.93). The combination of markers was a significant improvement over the prediction performance of HERB2 ($p<0.001$). (Table 3, FIG. 3)

We also performed a stratified analysis to check the relationship between HERB2 positivity and ERSRP in binary combinations, as shown in Table 3:

TABLE 3

| Brain metastasis markers of invention | HERB2 + | | | HERB2 − | | |
|---|---|---|---|---|---|---|
| | Sensibility | LRs + | $\chi^2$ | Specificity | LRs − | $\chi^2$ |
| GRP 94 | 8/8 (100) | 2.78 | 0.16 | 48/89 (53.9) | 2.31 | 0.14 |
| FN 14 | 5/8 (62.5) | 1.47 | 0.23 | 68/88 (77.3) | 6.88 | 0.004 |

TABLE 3-continued

| Brain metastasis markers of invention | HERB2 + | | | HERB2 − | | |
|---|---|---|---|---|---|---|
| | Sensibility | LRs + | $\chi^2$ | Specificity | LRs − | $\chi^2$ |
| TRAF 2 | 6/7 (85.7) | 0.54 | 0.46 | 36/71 (50.7) | 1.06 | 0.27 |
| Traditional markers | | | | | | |
| ER | 3/7 (42.9) | 0.54 | 0.46 | 21/83 (25.3) | 1.06 | 0.27 |
| PR | 2/7 (28.6) | 0.43 | 0.56 | 29/81 (35.8) | 2.43 | 0.11 |
| HG III | 6/8 (75.0) | 0.14 | 0.71 | 42/45 (93.3) | 0.77 | 0.39 |

In HERB2 negative tumors, FN14 had a high negative likelihood ratio to predict the absence of brain metastasis progression (LR=0.26, sensibility=0.8, p=0.015). Moreover, if the best predictor of brain metastasis alone was HERB-2, the addition of GRP94, TRAF2 and FN14 expression significantly increased the prediction of metastatic disease in brain. Furthermore, the combination of GRP94, FN14, Inhibin and HERB-2 showed a prediction of metastatic disease in brain aROC=0.90.

The invention claimed is:

1. A method for treating brain metastasis in a subject diagnosed with a breast tumor, the method comprising: (a) determining the level of expression of GRP94, FN14 or both in a breast tumor sample isolated from said subject; (b) detecting overexpression of GRP94, FN14 or both in the breast tumor sample relative to the level of said GRP94, FN14 or both in a control sample; and (c) treating brain metastasis in the subject detected to have an over-expression of GRP94, FN14 or both.

2. The method according to claim 1, wherein the level of expression of GRP94 and FN14 is determined.

3. The method according to claim 1, which further comprises determining the level of expression of inhibin.

4. The method according to claim 3, wherein the level of expression of the set of markers GRP94, FN14 and Inhibin is determined.

5. The method according to claim 3, which further comprises determining the level of expression of HERB2.

6. The method according to claim 5, wherein the level of expression of the set of markers GRP94, FN14 and HERB2 is determined.

7. The method according to claim 6, wherein the level of expression of the set of markers GRP94, FN14, inhibin and HERB-2 is determined.

8. The method according to claim 1, which further comprises determining the level of expression of TRAF-2.

9. The method according to claim 8, wherein the level of expression of the set of markers GRP94, FN14 and TRAF-2 is determined.

10. The method according to claim 4, which further comprises determining the level of expression of HERB2.

11. The method according to claim 10, wherein the level of expression of the set of markers GRP94, TRAF-2, Inhibin, HERB2, and FN14 is determined.

12. The method according to claim 10, which further comprises determining the level of expression of TRAF-2.

13. The method according to claim 1, wherein the determination of the level of GRP94, FN14 or both comprises determining the amount of protein of GRP94, FN14, or both.

14. The method according to claim 13, wherein the amount of protein is determined using an antibody which specifically binds to said protein.

15. The method according to claim 14, wherein the antibody is used to perform immunohistochemistry.

16. The method according to claim 1, wherein the determination of the level of GRP94, FN14 or both comprises determining the amount of mRNA of GRP94, FN14 or both.

* * * * *

```
SEQUENCE LISTING

<160> NUMBER OF SEQ ID NOS: 5

<210> SEQ ID NO 1
<211> LENGTH: 803
<212> TYPE: PRT
<213> ORGANISM: Homo sapiens
<300> PUBLICATION INFORMATION:
<308> DATABASE ACCESSION NUMBER: Swiss-Prot/P14625
<309> DATABASE ENTRY DATE: 1990-04-01
<313> RELEVANT RESIDUES IN SEQ ID NO: (1)..(803)

<400> SEQUENCE: 1

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190
```

-continued

```
Gly Gln Phe Gly Val Gly Phe Tyr Ser Ala Phe Leu Val Ala Asp Lys
            195                 200                 205
Val Ile Val Thr Ser Lys His Asn Asn Asp Thr Gln His Ile Trp Glu
    210                 215                 220
Ser Asp Ser Asn Glu Phe Ser Val Ile Ala Asp Pro Arg Gly Asn Thr
225                 230                 235                 240
Leu Gly Arg Gly Thr Thr Ile Thr Leu Val Leu Lys Glu Glu Ala Ser
                245                 250                 255
Asp Tyr Leu Glu Leu Asp Thr Ile Lys Asn Leu Val Lys Lys Tyr Ser
            260                 265                 270
Gln Phe Ile Asn Phe Pro Ile Tyr Val Trp Ser Ser Lys Thr Glu Thr
        275                 280                 285
Val Glu Glu Pro Met Glu Glu Glu Ala Ala Lys Glu Glu Lys Glu
    290                 295                 300
Glu Ser Asp Asp Glu Ala Ala Val Glu Glu Glu Glu Glu Lys Lys
305                 310                 315                 320
Pro Lys Thr Lys Lys Val Glu Lys Thr Val Trp Asp Trp Glu Leu Met
                325                 330                 335
Asn Asp Ile Lys Pro Ile Trp Gln Arg Pro Ser Lys Glu Val Glu Glu
            340                 345                 350
Asp Glu Tyr Lys Ala Phe Tyr Lys Ser Phe Lys Glu Ser Asp Asp
        355                 360                 365
Pro Met Ala Tyr Ile His Phe Thr Ala Glu Gly Glu Val Thr Phe Lys
    370                 375                 380
Ser Ile Leu Phe Val Pro Thr Ser Ala Pro Arg Gly Leu Phe Asp Glu
385                 390                 395                 400
Tyr Gly Ser Lys Lys Ser Asp Tyr Ile Lys Leu Tyr Val Arg Arg Val
                405                 410                 415
Phe Ile Thr Asp Asp Phe His Asp Met Met Pro Lys Tyr Leu Asn Phe
            420                 425                 430
Val Lys Gly Val Val Asp Ser Asp Asp Leu Pro Leu Asn Val Ser Arg
        435                 440                 445
Glu Thr Leu Gln Gln His Lys Leu Leu Lys Val Ile Arg Lys Lys Leu
    450                 455                 460
Val Arg Lys Thr Leu Asp Met Ile Lys Lys Ile Ala Asp Asp Lys Tyr
465                 470                 475                 480
Asn Asp Thr Phe Trp Lys Glu Phe Gly Thr Asn Ile Lys Leu Gly Val
                485                 490                 495
Ile Glu Asp His Ser Asn Arg Thr Arg Leu Ala Lys Leu Leu Arg Phe
            500                 505                 510
Gln Ser Ser His His Pro Thr Asp Ile Thr Ser Leu Asp Gln Tyr Val
        515                 520                 525
Glu Arg Met Lys Glu Lys Gln Asp Lys Ile Tyr Phe Met Ala Gly Ser
    530                 535                 540
Ser Arg Lys Glu Ala Glu Ser Ser Pro Phe Val Glu Arg Leu Leu Lys
545                 550                 555                 560
Lys Gly Tyr Glu Val Ile Tyr Leu Thr Glu Pro Val Asp Glu Tyr Cys
                565                 570                 575
Ile Gln Ala Leu Pro Glu Phe Asp Gly Lys Arg Phe Gln Asn Val Ala
            580                 585                 590
Lys Glu Gly Val Lys Phe Asp Glu Ser Glu Lys Thr Lys Glu Ser Arg
        595                 600                 605
Glu Ala Val Glu Lys Glu Phe Glu Pro Leu Leu Asn Trp Met Lys Asp
```

```
                610             615             620
Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
                660                 665                 670

Ile Ser Thr Asn Tyr Tyr Ala Ser Gln Lys Lys Thr Phe Glu Ile Asn
                675                 680                 685

Pro Arg His Pro Leu Ile Arg Asp Met Leu Arg Arg Ile Lys Glu Asp
690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
                740                 745                 750

Ala Lys Val Glu Glu Pro Glu Glu Pro Glu Glu Thr Ala Glu
                755                 760                 765

Asp Thr Thr Glu Asp Thr Glu Gln Asp Glu Glu Met Asp Val
770                 775                 780

Gly Thr Asp Glu Glu Glu Thr Ala Lys Glu Ser Thr Ala Glu Lys
785                 790                 795                 800

Asp Glu Leu

<210> SEQ ID NO 2
<211> LENGTH: 129
<212> TYPE: PRT
<213> ORGANISM: Homo sapiens
<300> PUBLICATION INFORMATION:
<308> DATABASE ACCESSION NUMBER: Swiss-Prot/Q9NP84
<309> DATABASE ENTRY DATE: 2000-10-01
<313> RELEVANT RESIDUES IN SEQ ID NO: (1)..(129)

<400> SEQUENCE: 2

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
                35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Ala Val Ala Leu Ile
                115                 120                 125

Gln

<210> SEQ ID NO 3
<211> LENGTH: 501
<212> TYPE: PRT
```

<213> ORGANISM: Homo sapiens
<300> PUBLICATION INFORMATION:
<308> DATABASE ACCESSION NUMBER: Swiss-Prot/Q96NT2
<309> DATABASE ENTRY DATE: 2002-09-19
<313> RELEVANT RESIDUES IN SEQ ID NO: (1)..(501)

<400> SEQUENCE: 3

```
Met Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
                20                  25                  30

Leu Cys Ser Ala Cys Arg Asn Val Leu Arg Arg Pro Phe Gln Ala Gln
                35                  40                  45

Cys Gly His Arg Tyr Cys Ser Phe Cys Leu Ala Ser Ile Leu Ser Ser
        50                  55                  60

Gly Pro Gln Asn Cys Ala Ala Cys Val His Gly Ile Tyr Glu Glu
65                  70                  75                  80

Gly Ile Ser Ile Leu Glu Ser Ser Ser Ala Phe Pro Asp Asn Ala Ala
                85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
            115                 120                 125

Cys Pro Leu Met Leu Thr Glu Cys Pro Ala Cys Lys Gly Leu Val Arg
            130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
            195                 200                 205

Cys Gly Lys Cys Arg Val Pro Cys Arg Phe His Ala Ile Gly Cys Leu
            210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Arg Cys
                260                 265                 270

Glu Ser Leu Glu Lys Lys Thr Ala Thr Phe Glu Asn Ile Val Cys Val
            275                 280                 285

Leu Asn Arg Glu Val Glu Arg Val Ala Met Thr Ala Glu Ala Cys Ser
            290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Leu Glu Met Glu Ala Ser Thr Tyr Asp Gly
                340                 345                 350

Val Phe Ile Trp Lys Ile Ser Asp Phe Ala Arg Lys Arg Gln Glu Ala
            355                 360                 365

Val Ala Gly Arg Ile Pro Ala Ile Phe Ser Pro Ala Phe Tyr Thr Ser
            370                 375                 380
```

-continued

```
Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
            405                 410                 415

Pro Asn Asp Ala Leu Leu Arg Trp Pro Phe Asn Gln Lys Val Thr Leu
        420                 425                 430

Met Leu Leu Asp Gln Asn Asn Arg Glu His Val Ile Asp Ala Phe Arg
    435                 440                 445

Pro Asp Val Thr Ser Ser Phe Gln Arg Pro Val Asn Asp Met Asn
450                 455                 460

Ile Ala Ser Gly Cys Pro Leu Phe Cys Pro Val Ser Lys Met Glu Ala
465                 470                 475                 480

Lys Asn Ser Tyr Val Arg Asp Asp Ala Ile Phe Ile Lys Ala Ile Val
                485                 490                 495

Asp Leu Thr Gly Leu
            500

<210> SEQ ID NO 4
<211> LENGTH: 1255
<212> TYPE: PRT
<213> ORGANISM: Homo sapiens
<300> PUBLICATION INFORMATION:
<308> DATABASE ACCESSION NUMBER: Swiss-Prot/P04626
<309> DATABASE ENTRY DATE: 2002-09-19
<313> RELEVANT RESIDUES IN SEQ ID NO: (1)..(1255)

<400> SEQUENCE: 4

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
```

-continued

```
                645                 650                 655
Ala Val Val Gly Ile Leu Leu Val Val Leu Gly Val Val Phe Gly
                    660                 665                 670
Ile Leu Ile Lys Arg Arg Gln Gln Lys Ile Arg Lys Tyr Thr Met Arg
                675                 680                 685
Arg Leu Leu Gln Glu Thr Glu Leu Val Glu Pro Leu Thr Pro Ser Gly
            690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                    725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
        770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                        805                 810                 815
Leu Gly Ser Gln Asp Leu Leu Asn Trp Cys Met Gln Ile Ala Lys Gly
                    820                 825                 830
Met Ser Tyr Leu Glu Asp Val Arg Leu Val His Arg Asp Leu Ala Ala
                835                 840                 845
Arg Asn Val Leu Val Lys Ser Pro Asn His Val Lys Ile Thr Asp Phe
        850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                        885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
            915                 920                 925
Arg Glu Ile Pro Asp Leu Leu Glu Lys Gly Glu Arg Leu Pro Gln Pro
        930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                    965                 970                 975
Ser Arg Met Ala Arg Asp Pro Gln Arg Phe Val Val Ile Gln Asn Glu
                980                 985                 990
Asp Leu Gly Pro Ala Ser Pro Leu Asp Ser Thr Phe Tyr Arg Ser Leu
            995                 1000                1005
Leu Glu Asp Asp Asp Met Gly Asp Leu Val Asp Ala Glu Glu Tyr
        1010                1015                1020
Leu Val Pro Gln Gln Gly Phe Phe Cys Pro Asp Pro Ala Pro Gly
        1025                1030                1035
Ala Gly Gly Met Val His His Arg His Arg Ser Ser Ser Thr Arg
        1040                1045                1050
Ser Gly Gly Gly Asp Leu Thr Leu Gly Leu Glu Pro Ser Glu Glu
        1055                1060                1065
```

```
Glu Ala Pro Arg Ser Pro Leu Ala Pro Ser Glu Gly Ala Gly Ser
    1070            1075                1080

Asp Val Phe Asp Gly Asp Leu Gly Met Gly Ala Ala Lys Gly Leu
    1085            1090                1095

Gln Ser Leu Pro Thr His Asp Pro Ser Pro Leu Gln Arg Tyr Ser
    1100            1105                1110

Glu Asp Pro Thr Val Pro Leu Pro Ser Glu Thr Asp Gly Tyr Val
    1115            1120                1125

Ala Pro Leu Thr Cys Ser Pro Gln Pro Glu Tyr Val Asn Gln Pro
    1130            1135                1140

Asp Val Arg Pro Gln Pro Pro Ser Pro Arg Glu Gly Pro Leu Pro
    1145            1150                1155

Ala Ala Arg Pro Ala Gly Ala Thr Leu Glu Arg Pro Lys Thr Leu
    1160            1165                1170

Ser Pro Gly Lys Asn Gly Val Val Lys Asp Val Phe Ala Phe Gly
    1175            1180                1185

Gly Ala Val Glu Asn Pro Glu Tyr Leu Thr Pro Gln Gly Gly Ala
    1190            1195                1200

Ala Pro Gln Pro His Pro Pro Pro Ala Phe Ser Pro Ala Phe Asp
    1205            1210                1215

Asn Leu Tyr Tyr Trp Asp Gln Asp Pro Pro Glu Arg Gly Ala Pro
    1220            1225                1230

Pro Ser Thr Phe Lys Gly Thr Pro Thr Ala Glu Asn Pro Glu Tyr
    1235            1240                1245

Leu Gly Leu Asp Val Pro Val
    1250            1255

<210> SEQ ID NO 5
<211> LENGTH: 366
<212> TYPE: PRT
<213> ORGANISM: Homo sapiens
<300> PUBLICATION INFORMATION:
<308> DATABASE ACCESSION NUMBER: Swiss-Prot/P05111
<309> DATABASE ENTRY DATE: 1987-08-13
<313> RELEVANT RESIDUES IN SEQ ID NO: (1)..(366)

<400> SEQUENCE: 5

Met Val Leu His Leu Leu Leu Phe Leu Leu Leu Thr Pro Gln Gly Gly
1               5                   10                  15

His Ser Cys Gln Gly Leu Glu Leu Ala Arg Glu Leu Val Leu Ala Lys
                20                  25                  30

Val Arg Ala Leu Phe Leu Asp Ala Leu Gly Pro Pro Ala Val Thr Arg
            35                  40                  45

Glu Gly Gly Asp Pro Gly Val Arg Arg Leu Pro Arg Arg His Ala Leu
50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Glu Gly Leu Phe Arg
            100                 105                 110

Tyr Met Phe Arg Pro Ser Gln His Thr Arg Ser Arg Gln Val Thr Ser
        115                 120                 125

Ala Gln Leu Trp Phe His Thr Gly Leu Asp Arg Gln Gly Thr Ala Ala
    130                 135                 140
```

-continued

```
Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
            165                 170                 175

Ala Val Leu His Leu Ala Thr Ser Ala Leu Ser Leu Leu Thr His Pro
            180                 185                 190

Val Leu Val Leu Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
    210                 215                 220

Ser Gly Gly Glu Arg Ala Arg Arg Ser Thr Pro Leu Met Ser Trp Pro
225                 230                 235                 240

Trp Ser Pro Ser Ala Leu Arg Leu Leu Gln Arg Pro Pro Glu Glu Pro
            245                 250                 255

Ala Ala His Ala Asn Cys His Arg Val Ala Leu Asn Ile Ser Phe Gln
            260                 265                 270

Glu Leu Gly Trp Glu Arg Trp Ile Val Tyr Pro Pro Ser Phe Ile Phe
        275                 280                 285

His Tyr Cys His Gly Gly Cys Gly Leu His Ile Pro Pro Asn Leu Ser
    290                 295                 300

Leu Pro Val Pro Gly Ala Pro Pro Thr Pro Ala Gln Pro Tyr Ser Leu
305                 310                 315                 320

Leu Pro Gly Ala Gln Pro Cys Cys Ala Ala Leu Pro Gly Thr Met Arg
            325                 330                 335

Pro Leu His Val Arg Thr Thr Ser Asp Gly Gly Tyr Ser Phe Lys Tyr
            340                 345                 350

Glu Thr Val Pro Asn Leu Leu Thr Gln His Cys Ala Cys Ile
        355                 360                 365
```